United States Patent [19]
Koshino

[11] Patent Number: 5,766,251
[45] Date of Patent: Jun. 16, 1998

[54] WEDGE-SHAPED SPACER FOR CORRECTION OF DEFORMED EXTREMITIES

[75] Inventor: Tomihisa Koshino, 2-28-12, Maruyamadai, Kohnan-ku, Yokohama-shi, Kanagawa 233, Japan

[73] Assignee: Tomihisa Koshino, Kanagawa, Japan

[21] Appl. No.: 749,678

[22] Filed: Nov. 15, 1996

Related U.S. Application Data

[63] Continuation-in-part of Ser. No. 146,080, filed as PCT/JP93/00308, Mar. 15, 1993, abandoned.

[30] Foreign Application Priority Data

Mar. 13, 1992 [JP] Japan .................................. 4-55266

[51] Int. Cl.$^6$ .................................................. A61F 2/28
[52] U.S. Cl. ............................ 623/16; 623/17; 606/61
[58] Field of Search .............................. 623/16, 17–18, 623/20; 606/59–61, 63, 65, 67, 69–72, 88

[56] References Cited

U.S. PATENT DOCUMENTS

| | | | |
|---|---|---|---|
| 4,309,777 | 1/1982 | Patil | 623/17 |
| 4,624,673 | 11/1986 | Meyer | 623/16 |
| 4,743,256 | 5/1988 | Brantigan | 623/17 |
| 5,306,307 | 4/1994 | Senter et al. | 623/17 |
| 5,443,514 | 8/1995 | Steffee | 623/17 |
| 5,571,190 | 11/1996 | Ulrich et al. | 623/17 |

FOREIGN PATENT DOCUMENTS

60-150756  8/1985  Japan .

*Primary Examiner*—John G. Weiss
*Assistant Examiner*—Bruce E. Snow
*Attorney, Agent, or Firm*—Nikaido Marmelstein Murray & Oram LLP

[57] ABSTRACT

A wedge-shaped spacer usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia and, corrective osteotomy of the calcaneus, is made of a sintered hydroxyapatite provided with a plurality of pores having a pore size of 50 to 250 μm and connected with each other and with the outside through a plurality of capillaries having a thickness of 0.5 to 5 μm, and having a compression strength of 300 kg/cm$^2$ and a porosity of 30 to 50%, and which spacer has at least one thorn-shaped projection extending outwardly in a projecting direction from at least one of the upper and lower surface thereof, and at least one hole extending from the upper surface to the lower surface therethrough in parallel to the projecting direction of the thorn-shaped projection.

5 Claims, 2 Drawing Sheets

BEFORE OSTEOTOMY    AFTER OSTEOTOMY

BEFORE OSTEOTOMY   AFTER OSTEOTOMY

BEFORE OSTEOTOMY            AFTER OSTEOTOMY 5,766,251

1

WEDGE-SHAPED SPACER FOR CORRECTION OF DEFORMED EXTREMITIES

CROSS REFERENCE TO RELATED APPLICATION

This application is a continuation-in-part application of application Ser. No. 08/146,080, filed as PCT/JP93/00308, Mar. 15, 1993 now abandoned and also claims priority under 35 U.S.C. §120 PCT application Ser. No. PCT/JP93/00308, filed Mar. 15, 1993.

TECHNICAL FIELD

The present invention relates to a wedge-shaped spacer usable for correction of the deformed extremities due to bowlegs, knock knees, knee recurvatum, Blount's disease, rickets, osteonecrosis of the hips and the knees, Charcot joint, rheumatoid arthritis and osteoarthritis of the hips and the knees.

More particularly, the present invention relates to a wedge-shaped spacer usable for the correction of the deformed extremities to a normal limb form and alignment by inserting into the osteotomized portion formed by varus, valgus, flexion, extension and derotation osteotomies, such as corrective osteotomy for femoral shaft deformity, supracondylar osteotomy of the femur, intraarticular osteotomy of the femur, intraarticular osteotomy of the tibia, high tibial osteotomy, subtuberosity osteotomy of the tibia, and supramalleolar osteotomy of the calcaneus.

BACKGROUND ART

Among bowlegs, knock knees, knee recurvatum, Blount's disease, rickets, osteonecrosis of the hips and the knees, Charcot joint, rheumatoid arthritis and osteoarthritis of the hips and the knees, the osteoarthritis of the knee is a most common orthopaedic disease of middle-aged and older persons.

In an opening high tibial osteotomy which is an example of a surgical treatment for the osteoarthritis of the knee, it is necessary to graft bonechips from the patient to fill an opened space of the osteotomy site. For this necessity, there is a problem that fresh bonechips have to be taken from other sites of the patient body by another surgery. Also, there are problems that the bonechips from the patient to be grafted cannot be obtained in a desired form and the bone chips are hard to be obtained in the infants and the osteoporotic elderly; complications such as bleeding and infection occur in the donor site of the bonechips; even when desired bonechips can be taken, the grafted bonechips are absorbed and the remaining bone portion collapses and thus an expected result of correction is very hard to be obtained; and a complication such as infection occurs in the osteotomy site. If homograft is used, further problems occur such as infections, AIDS, immunological troubles. Under the above-mentioned circumstances, an attempt has been made to insert an artificial spacer material made by a metallic material or another material into the osteotomy site and to correct the deformed bone to a normal shape. Also, a method of gradually opening the osteotomy site by an external fixation has been attempted.

These conventional spacers have the following problems.

(1) Since the conventional spacer is inserted into and fixed in the osteotomy space only by a physical contact, the union of the operated bones is unable to be expected; and after the osteotomy, the patient is unable to start early exercises of joint motion and weightbearing walking; and a long rehabilitation time is required.

(2) The conventional spacer does not organically react with an organism and is not absorbed by the organism, and thus no vital tissue is regenerated, and the spacer remains as a foreign body in the vital tissue and causes various complications after the insertion.

(3) Therefore, the use of the conventional spacer causes a high risk of occurring of fracture or infection.

Also, surgical treatments using external fixation cause a very high risk of infection, skin injury and palsy due to nerve damage, and these diseases are difficult to be cured, requiring a long period of hospitalization.

DISCLOSURE OF THE INVENTION

An object of the present invention is to provide a wedge-shaped spacer usable for varus, valgus, flexion, extension and derotation osteotomies such as corrective osteotomy of femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, corrective osteotomy of the calcaneus, in surgical treatments for bowlegs, knock knees, knee recurvatum, Blount's disease, rickets, osteonecrosis of the femoral head and the knee, Charcot joint, rheumatoid arthritis and osteoarthritis of the hip and the knee. The spacer of the present invention is able to get rid of the abovementioned disadvantages of the conventional spacer used in varus, valgus, flexion, extension and derotation osteotomies such as corrective osteotomy for femoral shaft deformity, supracondylar osteotomy of femur, intraarticular osteotomy of femur, intraarticular osteotomy of tibia, high tibial osteotomy and subtuberosity osteotomy of tibia, supramalleolar osteotomy of the tibia, and corrective osteotomy of the calcaneus, and is capable of being securely fixed in the osteotomized portion between the fragments formed by the above-mentioned osteotomies.

Another object of the present invention is to provide a wedge-shaped spacer usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, and supramalleolar osteotomy of the tibia, corrective osteotomy of the calcaneus, which is capable of promoting the union of the osteotomized site so as to greatly shorten the necessary rehabilitation time and to enable the patient to start the early exercise of joint motion and weightbearing walking after the osteotomy, holding the movable range of the operated joint in a good condition, to enable the surrounding bones to be generated by stimulating the activity of the osteoblasts so as to regenerate the vital tissue.

In the present invention, the above-mentioned problems can be successfully solved by forming a wedgeshaped spacer, to be inserted into an osteotomized site formed by the varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, made of a specific sintered ceramic material having an excellent affinity to organism and a specific porous structure and provided with at least one thorn-shaped projection extending outwardly and at least one hole extending from the upper surface to the lower surface thereof through the spacer.

Namely, the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, comprises a sintering product of hydroxyapatite which is provided with a plurality of pores having a pore size of 50 to 250 μm and connected with each other and with the outside through a plurality of capillaries having a thickness of 0.5 to 5 μm, and has a compression strength of 300 kg/cm² and a porosity of 30 to 50%, and has an upper surface and a lower surface, at least one thorn-shaped projection extending outwardly from at least one of the upper and lower surface, and at least one hole extending from the upper surface to the lower surface through the wedge-shaped spacer.

In the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, the hole preferably has a polygonal cross-sectional profile.

Also, in the wedge-shaped spacer usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, and supramalleolar osteotomy of the tibia, corrective osteotomy of the calcaneus, the upper and lower surfaces of the wedge-shaped spacer are preferably inclined in relation to each other at an angle of 5 to 15 degrees.

Further in the wedge-shaped spacer usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, and supramalleolar osteotomy of the tibia, corrective osteotomy of the calcaneus, the thorn-shaped projection preferably has a height of from 2 to 4 mm.

Furthermore, in the wedge-shaped spacer usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, optionally, a plate member is attached to a head portion of the wedge-shaped spacer.

BEST MODE OF CARRYING OUT THE INVENTION

Figure 1:
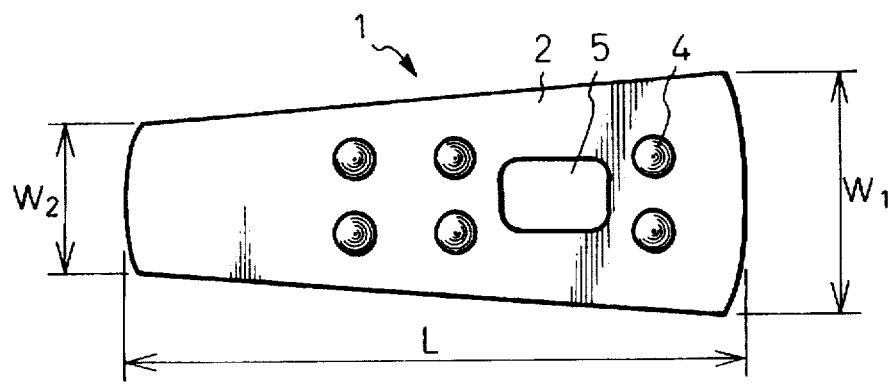
FIG. 1 is a plane view of an embodiment of the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus.
Figure 2:
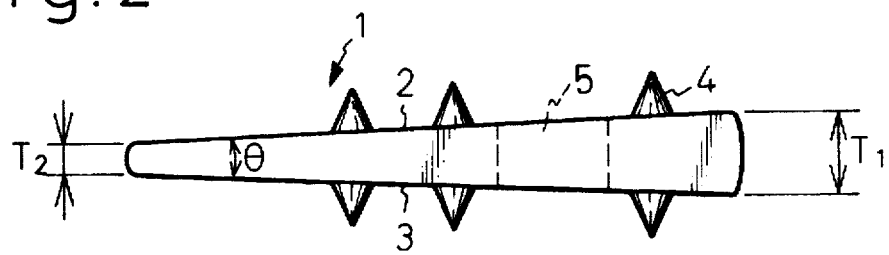
FIG. 2 is a front view of the wedge-shaped spacer of FIG. 1 usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus.

A plan view of an embodiment of the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, and supramalleolar osteotomy of the tibia, corrective osteotomy of the calcaneus., is shown in FIG. 1 and a front view of the spacer of FIG. 1 is shown in FIG. 2.

In FIGS. 1 and 2, a spacer 1 has a wedge-like form and is provided with an upper surface 2 and a lower surface 3 opposite to each other and inclined away from each other.

In the spacer 1 of the present invention, at least one, preferably 4 to 8 thorn-shaped projections 4 are formed on at least one, preferably both, of the upper and lower surface 2 and 3 in such a manner that the projections 4 extend outward from the surface or surfaces of the spacer. The thorn-shaped projections are very effective to securely fix the spacer to the bone fragments above and below the spacer within the osteotomized region and to enhance the bone union of the osteotomy site.

The secure fixation of the wedge-shaped spacer in the osteotomized region is very important for promoting the union of the bone tissue located above and below the wedge-shaped spacer with each other, which will be further explained hereinafter.

The dimensions and form of the thorn-shaped projections of the wedge-shaped spacer material of the present invention are not restricted to specific values and a specific form and the dimensions are variable depending on the dimensions and form of the osteotomized portion. Generally, the thorn-shaped projections have a height of 2 to 4 mm and are in any form such as a circular cone, trigonal pyramid, quadrangular pyramid, polygonal pyramid and elliptical cone. Preferably, the thorn-shaped projections have a sharpened top end so as to enable the spacer material to be firmly anchored to the bone fragments above and below the spacer in the osteotomized region.

Also, the wedge-shaped spacer 1 of the present invention usable for varus, valgus, flexion, extension and derotation osteotomies such as corrective osteotomy for femoral shaft deformity, supracondylar osteotomy of the femur, intraarticular osteotomy of the tibia, high tibial osteotomy and subtuberosity osteotomy of the tibia, supramalleolar osteotomy of the tibia, and corrective osteotomy of the calcaneus, is provided with at least one, preferably 1 to 6 holes 5 through which the upper surface 2 and lower surfaces 3 are connected to each other. The holes 5 are used for insertion of the small bonechips of the patient thereinto which are able to be obtained around the osteotomy site. When a wedgeshaped spacer 1 having the small bonechips inserted into the holes 5 is inserted into the osteotomized portion, the growth of bone is accelerated within a relatively short period so that the new bone formation of the inserted bonechips and the bone tissue located above and below the wedge-shaped spacer 1 are accelerated and these bones are united easily with each other. Further, the grafted bonechips inserted into the holes rapidly grow and are united with each other. Due to the abovementioned union of the newly formed bones, the stability of the wedge-shaped spacer 1 in the osteotomized portion is enhanced so as to ensure the regeneration of the surrounding vital tissue, reformation and union of the bone.

There are no specific limitations to the form and dimensions of the holes 5. The form and dimensions of the holes 5 may be appropriately established. Nevertheless, the holes 5 preferably have a polygonal cross-sectional profile, more preferably a rectangular cross-sectional profile. When the cross-sectional profile of the hole of the wedge-shaped spacer is polygonal, the small bonechips of the patient, which are obtained from the bone tissue around the osteotomy site and inserted into the hole, grow in the hole of the corresponding cross-sectional profile and are connected to the bone portions located above and below the spacer, and thus the spacer cannot rotate around the resultant shaft consisting of the grown bonechips with the polygonal cross-section, and can be maintained at the desired angle of correction without deviation. Also, in the case of derotation osteotomy, the tissues such as the muscle, the tendon, the ligament and the periosteum around the osteotomy site tend to be restored to the original state and thus rotational deformity tends to be recurred. The polygonal cross-section of the hole of the spacer effectively prevent the restoration of the axial rotation of the bone. The capability of the hole for stabilizing the osteotomized bones against restoration becomes highest when the hole has a rectangular cross-sectional profile.

Polygons other than a rectangle are closer to a circle and thus may allow the rotationally osteotomized bone parts to be slightly restored.

The corners of the holes with the polygonal cross-section are preferably slightly rounded. If sharply angled (not rounded), portions of the bonechip of the patient inserted into the hole with sharp corners have a reduced blood circulation in those corners and thus the bone tissue may have corner osteonecrosis.

The wedge-shaped spacer usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, and supramalleolar osteotomy of the tibia, corrective osteotomy of the calcaneus, are made of a sintering product of hydroxyapatite which is one of bioactive ceramics. The sintering product of hydroxyapatite usable for the present invention has a plurality of pores having a pore size of 50 to 250 µm, preferably 70 to 200 µm and connected to each other and to the outside thereof through a plurality of capillaries having a thickness of 0.5 to 5 µm, preferably 1 to 3 µm. These pores and capillaries can receive therein cells for the regeneration of the bone and prevent invasion of harmful substances, so as to promote the new formation of the bone and the regeneration of the surrounding vital tissues. Also, the spacer made by the above-mentioned porous hydroxyapatite sintering product can promote the union of the bone parts located above and below the wedge-shaped spacer with each other.

The hydroxyapatite comprises, as a principal component, a compound of the composition formula: $Ca_5(PO_4)_3OH$ or $Ca_{10}(PO_4)_6(OH)_2$, and some Ca atoms are optionally replaced by at least one member selected from, for example, Sr, Ba, Mg, Fe, Al, Y, La, Na, K and H. Also, a portion of ($PO_4$) groups is optionally at least one member selected from $VO_4$, $BO_3$, $SO_4$, $CO_3$, and $SiO_4$. The hydroxyapatite may be in the form of an ordinary crystal, isomorphism type solid solution, substitution type solid solution, or penetration type solid solution. Also, the hydroxyapatite may have a structure with a non-quantum theoretical lattice defect.

The pores formed in the sintered hydroxyapatite spacer are preferably in the forms of true spheres or balls. When the porous spacer is inserted into the osteotomized portion of the bone, the pores provide living spaces for biologically activate osteoclasts and osteoblasts. If the pore size is less than 50 µm or more than 250 µm, the resultant pores cannot be suitable living spaces for the above-mentioned cells. Also, pores having a size of more than 250 µm cause the resultant wedge-shaped spacer to exhibit a significantly reduced mechanical strength, and thus, after the osteotomy, the patient cannot start early walking with weightbearing, and the necessary rehabilitation time after the surgery cannot be shortened.

The capillaries formed in the sintered hydroxyapatite spacer effectively connect the pores to each other and to the outside of the spacer, and thus the osteoclasts, osteoblasts, red blood cells and body fluid can freely penetrate into the spacer through the capillary, and development of blood capillaries is promoted. However, the capillaries formed in the sintered hydroxyapatite spacer have a thickness of 0.5 to 5 µm, the osteoclasts and collagen fibers are hard to infiltrate into the spacer through the capillaries, and thus undesirable irregular growth of the collagen fibers can be prevented.

As mentioned above, the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, corrective osteotomy of the calcaneus, comprises a sintering product of hydroxyapatite which is a bioactive ceramic and has a specific porous structure. Therefore, the wedge-shaped spacer of the present invention can selectively receive the cells which serve as the seed cells for the new bone formation while preventing the infiltration of the harmful substances into the spacer, so that the growth of cells contributory to new bone formation is promoted, the regeneration of vital tissues, namely replacement of artificial implant by vital tissue is promoted, and the union of the bone parts located above and below the spacer to each other is ensured.

The wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, has a compression strength of at least 300 kg/cm$^2$, preferably 400 to 500 kg/cm$^2$ and the sintering hydroxyapatite product has a porosity of 30 to 50%, preferably 34 to 45%. Namely, since the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, is inserted into the osteotomy site, the compression strength of the spacer must be 300 kg/cm$^2$ or more. If it is not, the patient cannot start early walking exercise, with weightbearing until the osteotomized sites are completely replaced by newly formed bone, and thus the necessary rehabilitation time cannot be minimized.

To keep the compression strength of the sintering product of hydroxyapatite at a level of 300 kg/cm$^2$ or more, the porosity of the sintering product must be adjusted to 50% or less. Also, to provide the abovementioned living spaces for biologically activating the osteoclasts and osteoblasts and to promote the new bone formation, it is very important to adjust the porosity of the sintering product of hydroxyapatite to 30% or more.

There are no specific limitations to the dimensions and form of the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus.

The dimensions and form of the spacer are appropriately set forth in consideration of the dimensions and form of the osteotomy site of the bone. Nevertheless, the wedge-shaped spacer material of the present invention generally has a length L of 30 to 80 mm, a largest width $W_1$ of 10 to 25 mm, a smallest width $W_2$ of 5 to 15 mm, a largest thickness of 3 to 15 mm and a smallest thickness of 1 to 3 mm.

The sintering product of hydroxyapatite usable for the present invention can be produced, for example, by mixing a desired amount of hydroxyapatite particles with organic synthetic resin particles having a particle size of 50 to 250 μm in an amount corresponding to the desired porosity of the sintering product, shaping the mixture into desired form and dimensions, heating the resultant shaped article at a temperature of 200° to 800° C. to decompose away the organic synthetic resin particles and finally sintering the heated article at a temperature of 800° C. to 1350° C., preferably 1000° C. to 1200° C. in an oxygen-containing oxidative atmosphere.

In the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, the upper surface 2 is inclined from the lower surface 3 at an inclination angle θ. The inclination angle θ is preferably in the range from 5 to 15 degrees. When the inclination angle θ is within the above-mentioned range, the resultant spacer can be easily inserted into an osteotomized space of the bone and the opening angle (correction angle) of the osteotomy site can be adequately controlled by regulating the insertion angle of the spacer.

Figure 3:
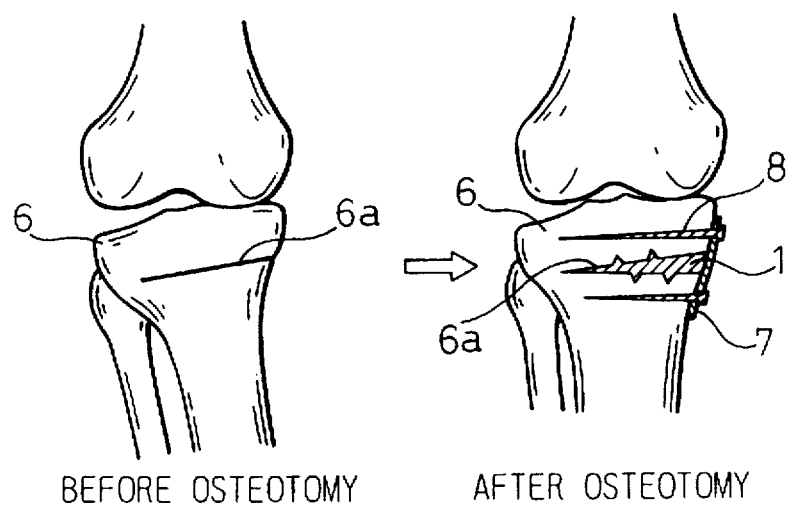
FIG. 3 is an explanatory view showing an employment condition of the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, when the spacer is employed for an opening high tibial osteotomy for the correction of bowlegs which is one of the most typical deformities in osteoarthritis of the knee.

Referring to FIG. 3, a portion 6a of the bone 6 is osteotomized and opened, and a wedge-shaped spacer 1 of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, is inserted into the osteotomized and opened 6a space of the bone 6, a head portion of the spacer 1 is held down by a metal or ceramic plate 7, and this plate 7 is fixed to the bone 6 by screws 8.

Figure 4:
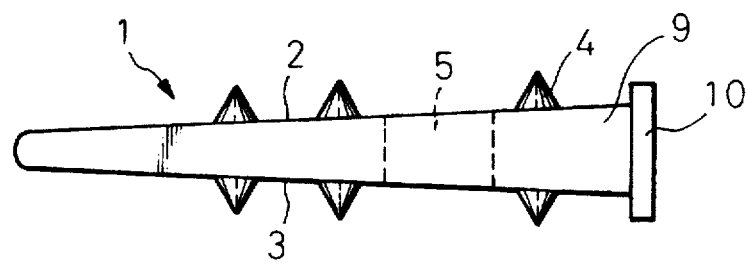
FIG. 4 is a front view of another embodiment of the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus.
Figure 5:
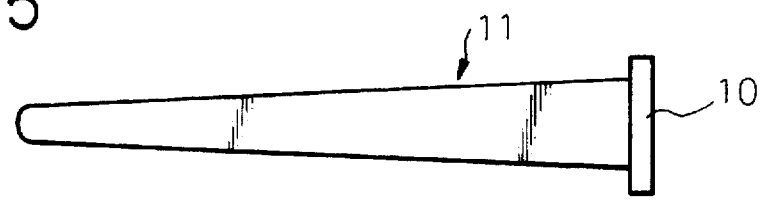
FIG. 5 is a front view of an embodiment of a correction angle-controlling spacer.

As shown in FIG. 4, the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, is optionally provided with a plate member 10 attached to a head portion 9 thereof having a largest thickness. The plate member 10 extends from the head portion 9 of the wedge-shaped spacer at a desired length (or area) in a desired direction or directions. When the wedge-shaped spacer is inserted into the osteotomized and opened space of the bone, the plate member 10 can be fixed to the bone by screws, and thereby the wedge-shaped spacer can be stabilized as a whole at a desired position in the bone.

Where the wedge-shaped spacer of the present invention usable for varus, valgus, flexion, extension and derotation osteotomies such as corrective osteotomy for femoral shaft deformity, supracondylar osteotomy of the femur, intraar- ticular osteotomy of the femur, intraarticular osteotomy of the tibia, high tibial osteotomy and subtuberosity osteotomy of the tibia, supramalleolar osteotomy of the tibia, and corrective osteotomy of the calcaneus, is inserted into osteotomized and opened space of the bone, in order to adjust the opening angle (correction angle) of the osteotomized and opened space to a desired value or in order to keep the wedge-shaped spacer of the present invention at the inserted position, a wedge-shaped member having no thorn-shaped projection, for example, a wedgeshaped member 11 as shown in FIG. 5 can be employed to control the correction angle. The wedge-shaped member 11 is optionally provided with a plate member 10 attached to a head portion thereof.

Figure 6:
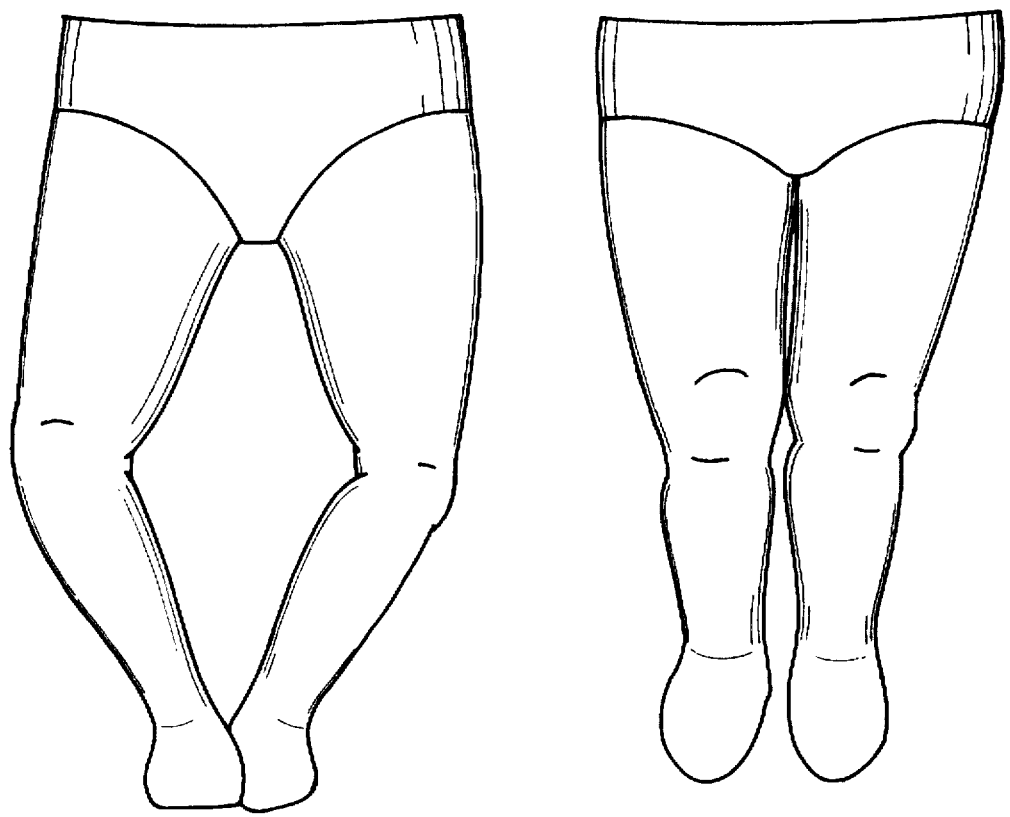
FIG. 6 is an explanatory view showing bow legs of the patient with osteoarthritis of the knee and its correction effect of the high tibial osteotomy using the wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia supramalleolar osteotomy of the tibia, and corrective osteotomy of the calcaneus.

The wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, can be utilized for the correction and treatment of bowlegs, knock knees, knee recurvatum, Blount's disease, rickets, osteonecrosis of the hips and the knees, Charcot joint, rheumatoid arthritis and osteoarthritis of the hips and the knees. When the wedge-shaped spacer of the present invention is used for the opening high tibial osteotomy for the osteoarthritis of the knee, the preoperative deformity of the lower extremities and joints can be corrected to normal shape (normal alignment), as shown in FIG. 6.

INDUSTRIAL APPLICABILITY

The wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, can be surely fixed to the osteotomized portion of the bone, and by controlling the horizontal direction and its angle of the insertion of the spacer material to an appropriate angle, the opening angle (correction angle) of the osteotomized space can be easily adjusted to a desired value. Therefore, the wedge-shaped spacer of the present invention is very useful for the correction and treatment of bowlegs, knock knees, knee recurvatum, Blount's disease, rickets, osteonecrosis of the hips and the knees, Charcot joint, rheumatoid arthritis and osteoarthritis of the hips and the knees.

The wedge-shaped spacer of the present invention usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, supramalleolar osteotomy of the tibia, and corrective osteotomy of the calcaneus, is provided with at least one hole extending from the upper surface to the lower surface thereof and formed from the sintering product of hydroxyapatite with a specific porous structure and a high compression strength, and thus is advantageous in that the bone union is extremely promoted, the patient can start weightbearing walking at a relatively earlier stage after the surgery, the movable range of the joint can be well maintained, the time necessary for rehabilitation after the surgery can be significantly shortened, and the occurrence of complications can be prevented.

Since the wedge-shaped spacer usable for varus, valgus, flexion, extension and derotation osteotomies such as corrective osteotomy for femoral shaft deformity, supracondylar osteotomy of the femur, intraarticular osteotomy of the femur, intraarticular osteotomy of the tibia, high tibial osteotomy and subtuberosity osteotomy of the tibia, and supramalleolar osteotomy of the tibia, corrective osteotomy of the calcaneus, can be absorbed and replaced by a newly formed bone, the spacer does not become a dead structure and does not cause any occurrence of various complications after the surgery.

I claim:

1. A wedge-shaped spacer usable for varus, valgus, flexion, extension and derotation osteotomies comprising a sintering product of hydroxyapatite which is provided with a plurality of pores having a pore size of 50 to 250 µm and connected with each other and with the outside through a plurality of capillaries having a thickness of 0.5 to 5 µm, and has a compression strength of 300 kg/cm$^2$ and a porosity of 30 to 50%, and having an upper surface and a lower surface, at least one thorn-shaped projection extending outwardly in a projecting direction from at least one of the upper and lower surface, and at least one hole extending from the upper surface to the lower surface through the wedge-shaped spacer in parallel to the projecting direction of the thorn-shaped projection.

2. The wedge-shaped spacer of claim 1 usable for varus, valgus, flexion, extension and derotation osteotomies wherein the hole has a polygonal cross-sectional profile.

3. The wedge-shaped spacer of claim 1 usable for varus, valgus, flexion, extension and derotation osteotomies wherein the upper and lower surfaces of the wedge-shaped spacer are inclined in relation to each other at an angle of 5 to 15 degrees.

4. The wedge-shaped spacer of claim 1 usable for varus, valgus, flexion, extension and derotation osteotomies wherein the thorn-shaped projection has a height of 2 to 4 mm.

5. The wedge-shaped spacer of claim 1 usable for varus, valgus, flexion, extension and derotation osteotomies wherein a plate member is attached to a head portion of the wedge-shaped spacer.

* * * * *